United States Patent [19]
Green et al.

[11] Patent Number: 5,392,979
[45] Date of Patent: * Feb. 28, 1995

[54] SURGICAL STAPLER APPARATUS

[75] Inventors: David T. Green, Westport; Henry Bolanos, Norwalk; Keith Ratcliff, Sandy Hook, all of Conn.

[73] Assignee: United States Surgical Corporation, Norwalk, Conn.

[*] Notice: The portion of the term of this patent subsequent to Jun. 9, 2009 has been disclaimed.

[21] Appl. No.: 151,398

[22] Filed: Nov. 12, 1993

Related U.S. Application Data

[63] Continuation of Ser. No. 622,943, Dec. 6, 1990, Pat. No. 5,285,944, which is a continuation of Ser. No. 54,328, May 26, 1987, Pat. No. 5,119,983.

[51] Int. Cl.$^6$ .......................................... A61B 17/115
[52] U.S. Cl. ...................................... 227/179; 227/19
[58] Field of Search ................ 227/179, 19, 175, 176, 227/180

[56] References Cited

U.S. PATENT DOCUMENTS

| | | |
|---|---|---|
| 317,154 | 5/1885 | Lowrie . |
| 3,193,165 | 7/1965 | Akhalaya et al. . |
| 3,270,124 | 8/1966 | Rawls et al. . |
| 3,388,847 | 6/1968 | Kasulin et al. . |
| 3,593,903 | 7/1971 | Astafiev et al. . |
| 4,043,685 | 8/1977 | Hyams . |
| 4,198,982 | 4/1980 | Fortner et al. . |
| 4,354,628 | 10/1982 | Green ........................... 227/19 |
| 4,476,863 | 10/1984 | Kanshin et al. . |
| 4,505,272 | 3/1985 | Ulyamyshev et al. . |
| 4,603,693 | 8/1986 | Conta et al. . |
| 4,654,030 | 3/1987 | Moll . |
| 4,697,948 | 10/1987 | Fukuda . |
| 4,733,987 | 3/1988 | Tomlinson et al. . |
| 4,817,847 | 4/1989 | Redtenbacher . |
| 4,848,367 | 7/1989 | Avant et al. . |
| 4,873,977 | 10/1989 | Avant et al. . |
| 5,119,983 | 6/1992 | Green et al. ................... 227/179 |
| 5,158,222 | 10/1992 | Green et al. ................... 227/19 X |

FOREIGN PATENT DOCUMENTS

| | | |
|---|---|---|
| 1136020 | 11/1982 | Canada . |
| 0282157 | 9/1988 | European Pat. Off. . |
| 1461464 | 12/1966 | France . |
| 1588250 | 4/1970 | France . |
| 2443239 | 7/1980 | France . |
| 1057729 | 5/1959 | Germany . |
| 3301713 | 11/1989 | Germany . |
| 7711347 | 10/1977 | Netherlands . |
| 8706448 | 11/1987 | WIPO . |
| WO06085 | 6/1990 | WIPO . |

OTHER PUBLICATIONS

Resnick, S. D., et al; Use of The Stapler in Anterior Resection For Cancer of The Rectosigmoid, Isreal Journal of Medical Sciences, vol. 19, 1983, pp. 128–133.

EEA Anvil with Separate Short Shaft—Non-Confidential Disclosure Agreement (Sep. 17, 1981), Professor S. (Simon) Resnick.

Catalog, TRUARC Beveled Retaining Rings. (undated).

Resnick, S.; New Method of Bowel Stoma Formation, Amer. Journal of Surgery, vol. 152, Nov. 1986, pp. 545–548.

Instruction Booklet—Tube Shaped Digestive Trace Stapling Instrument (undated) Specification.

*Primary Examiner*—Rinaldi I. Rada

[57] ABSTRACT

The end-to-end anastomosis apparatus is provided with a mounting means which can receive a trocar for making holes in tissue and, subsequently, an anvil shaft for the mounting of an anvil assembly for stapling purposes. The anvil shaft is provided with splines which cooperate with splines on a shell liner within the housing of the apparatus to align the buckets on the anvil assembly with the staples in a cartridge secured in the apparatus. In addition, the anvil assembly is provided with a spring for locking of the anvil housing on the anvil shaft.

27 Claims, 5 Drawing Sheets

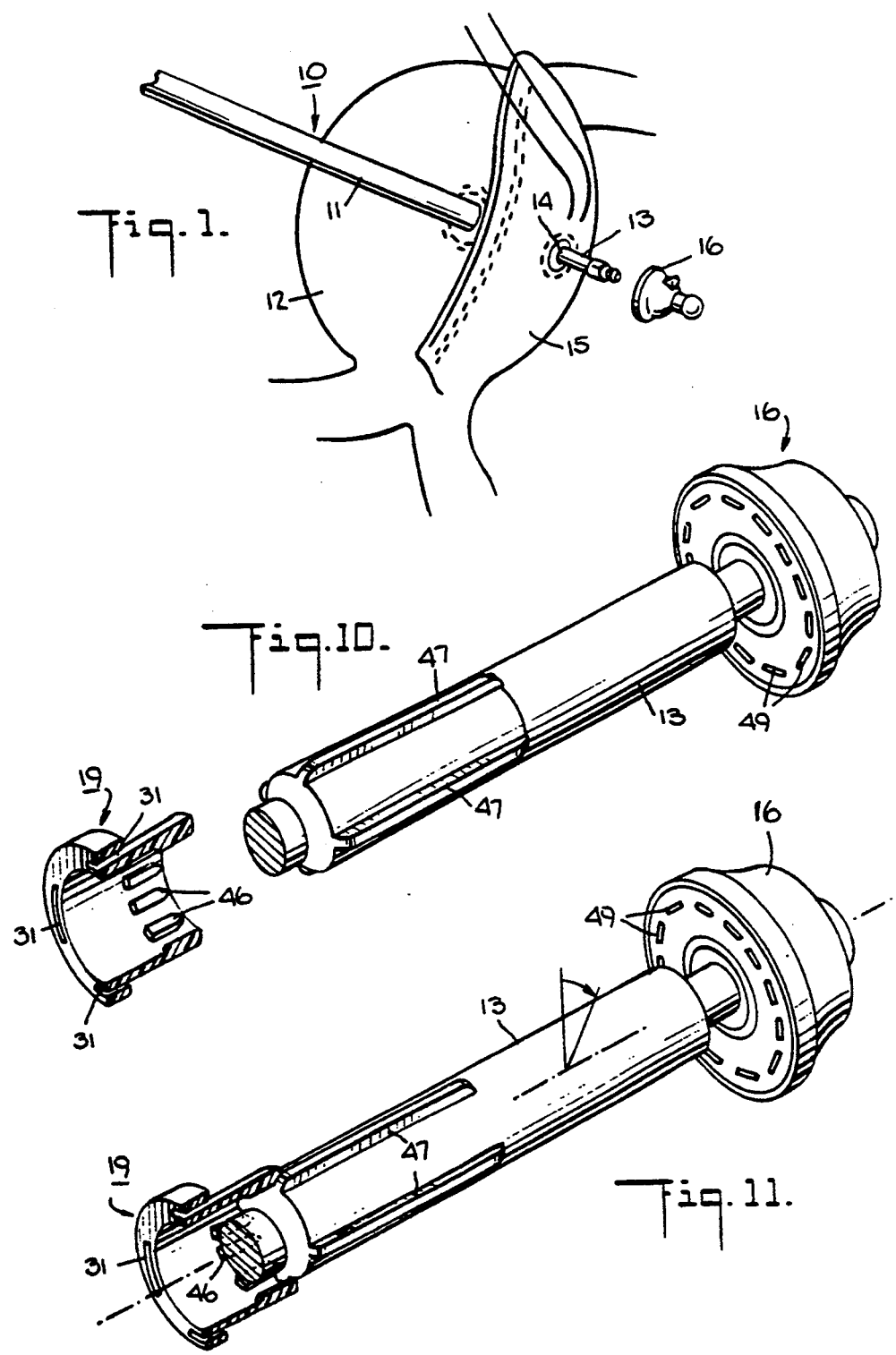

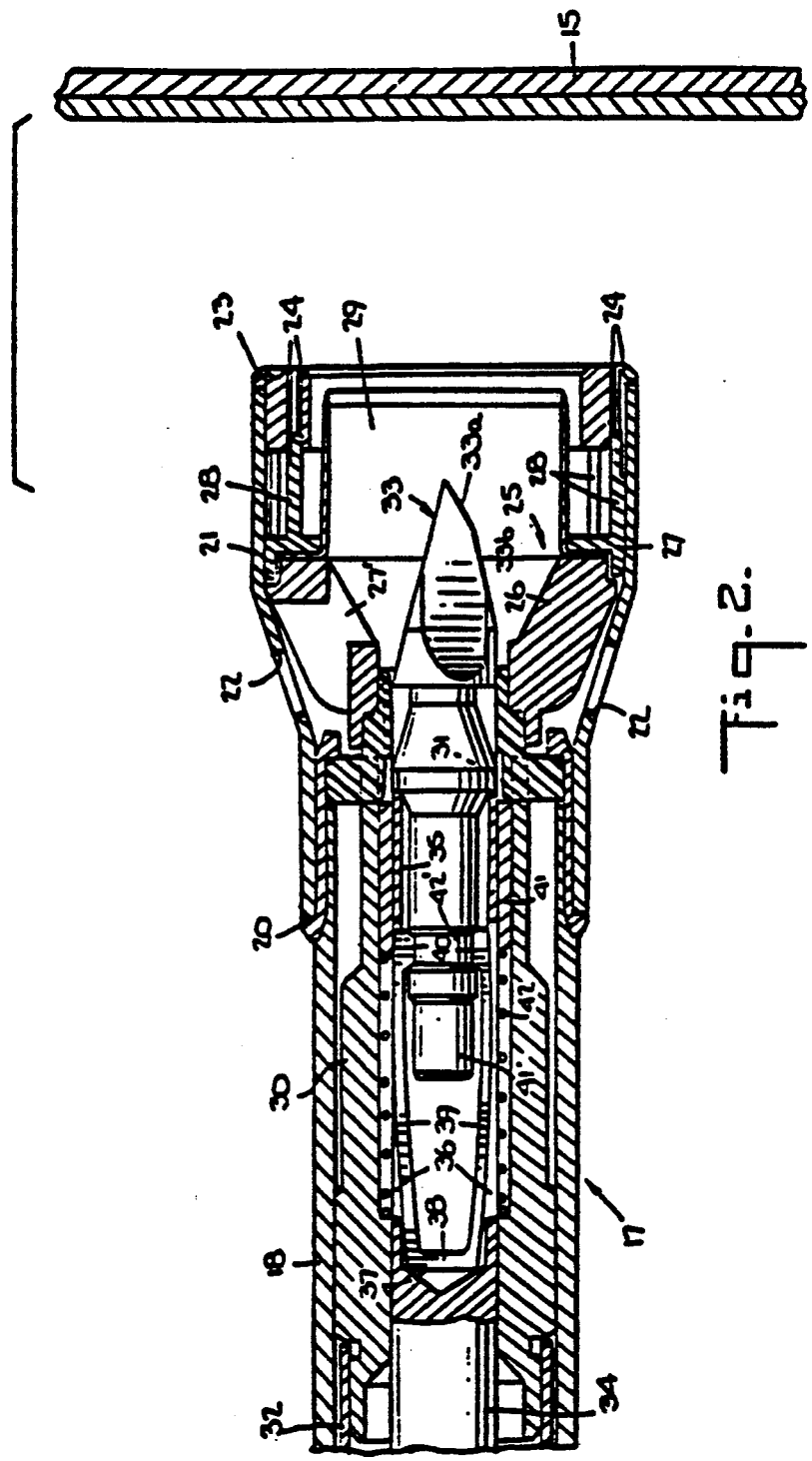

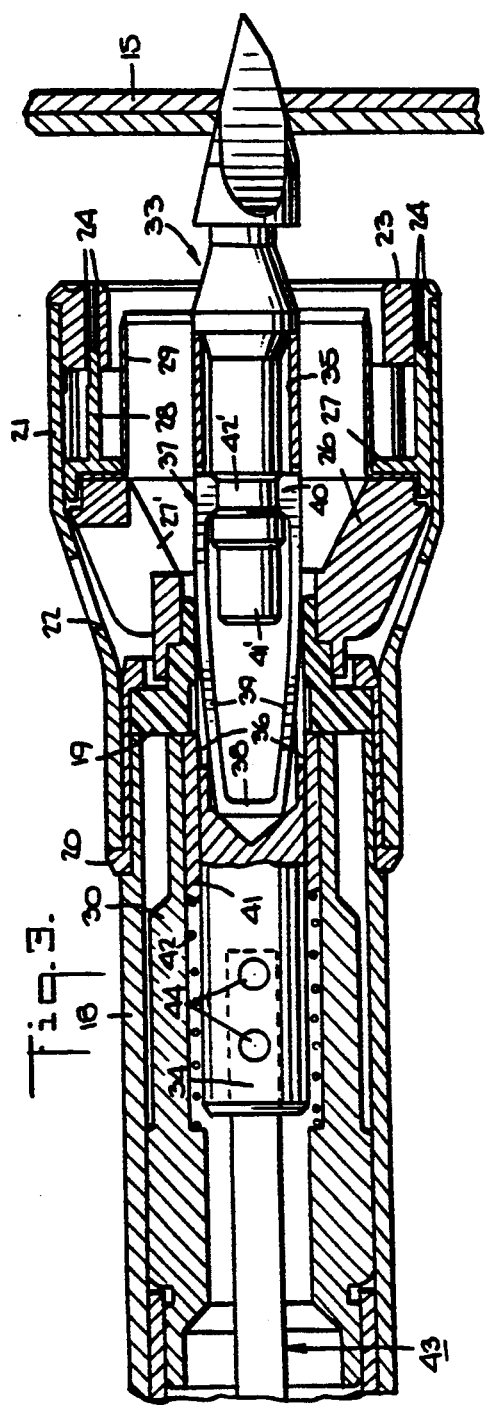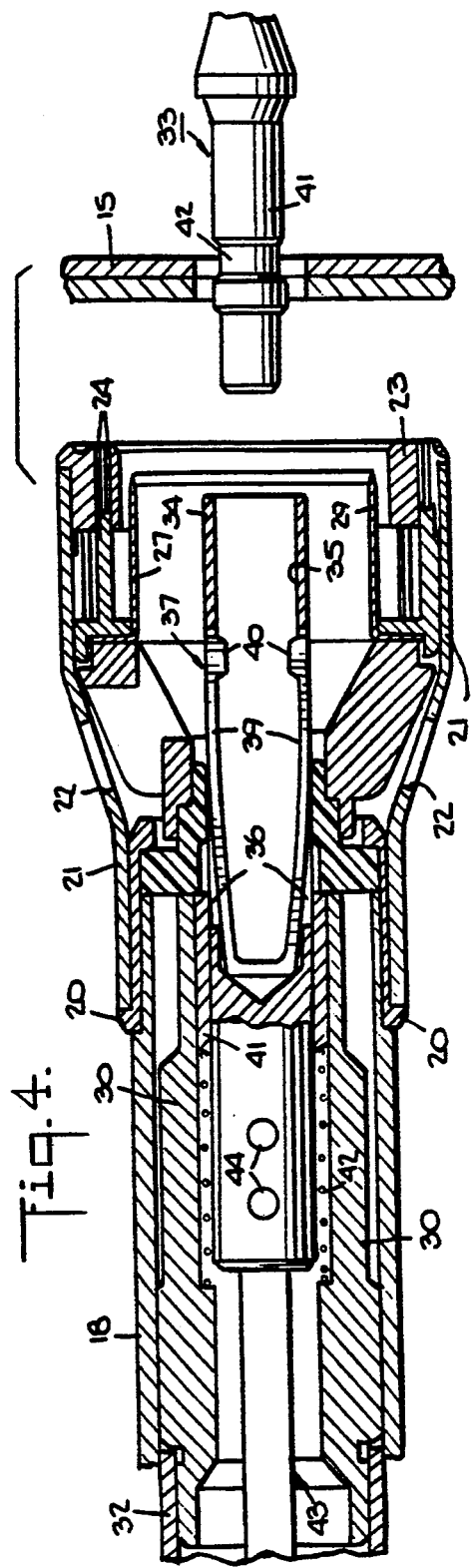

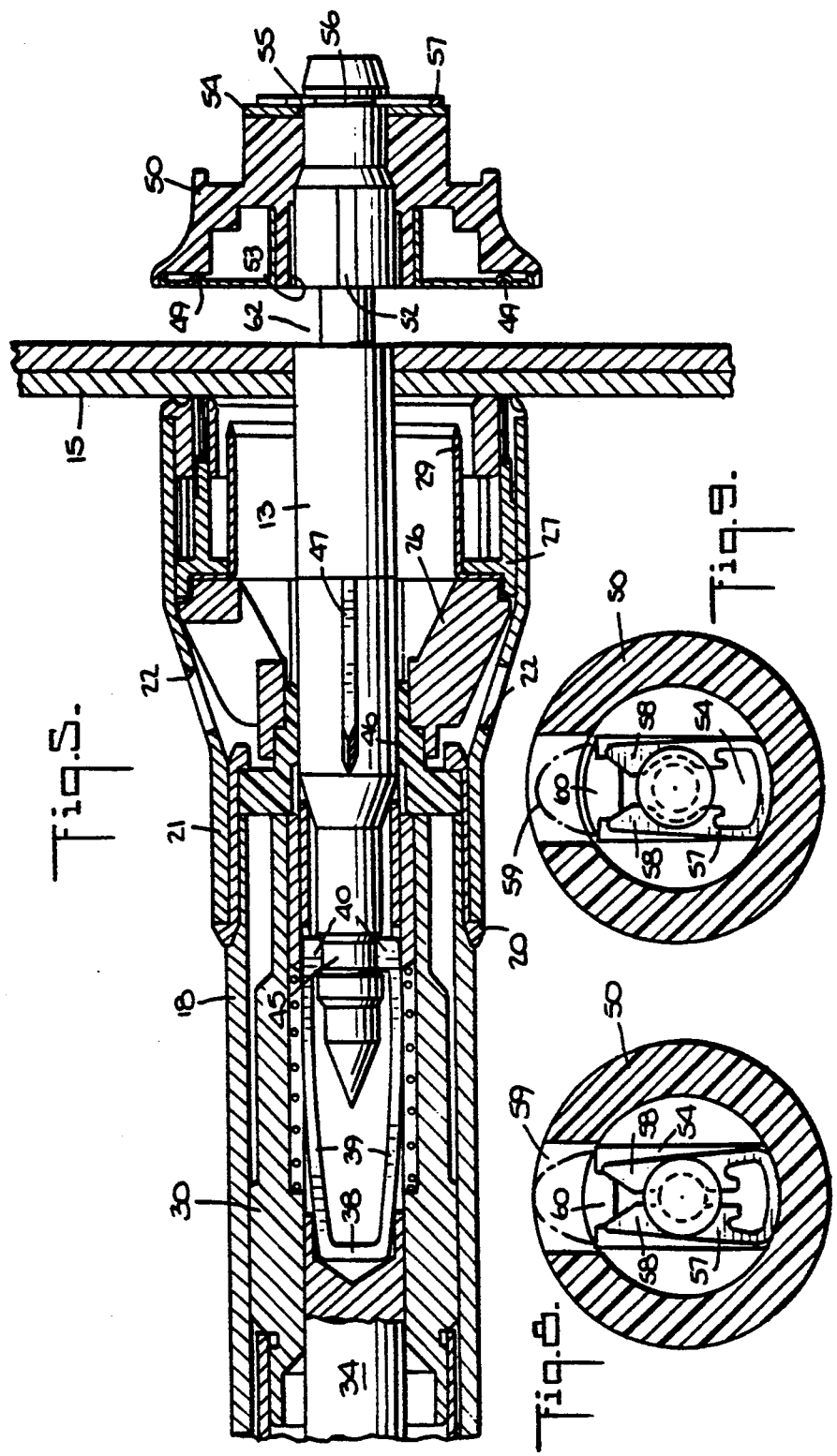

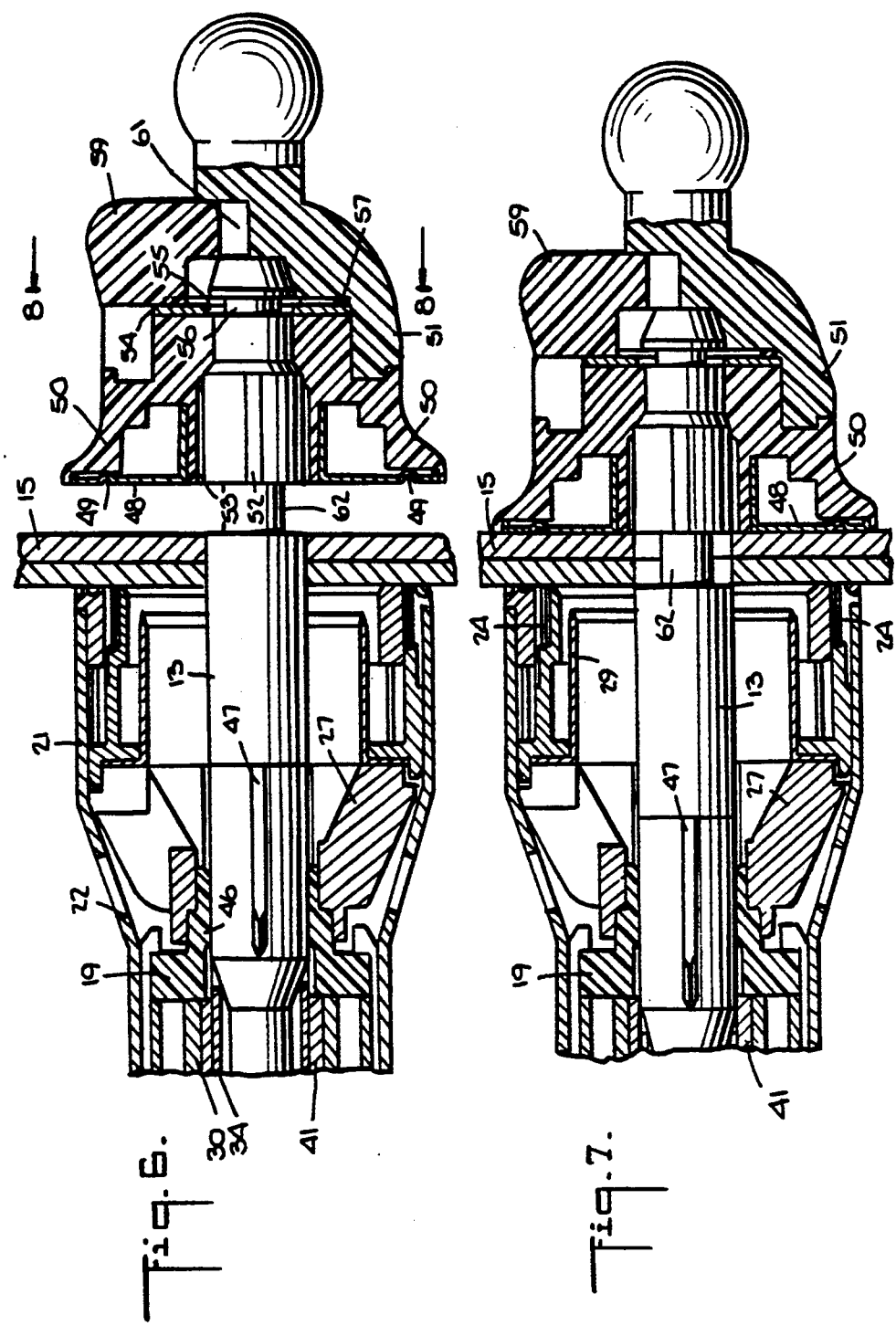

SURGICAL STAPLER APPARATUS

This is a continuation, of U.S. application Ser. No. 07/622,943 filed Dec. 6, 1990, now U.S. Pat. No. 5,285,944, which is a continuation, of U.S. application Ser. No. 07/054,328, filed May 26, 1987, now U.S. Pat. No. 5,119,983.

Heretofore, various types of surgical stapler apparati have been known for the application of staples to tissue. For example, it has been known to use various types of staplers in gastric and esophageal surgery, for example in both classic or modified gastric reconstructions performed end-to-end, end-to-side or side-to-side. In some cases, it has been known to create an anastomosis utilizing an instrument such as a Model EEA instrument manufactured by United States Surgical Corporation or like instruments where an anvil assembly can be threadably mounted on the threaded end of a central rod which can be retracted within a tubular housing of the instrument. In some cases, such an instrument is introduced into the lumen of a stomach without the anvil in place. Thereafter, the threaded tip of the center rod is passed through an opening which has been made at the anastomotic site so that the anvil can then be mounted on the end of the threaded rod. Subsequently, the anvil can be inserted into the duodeum, and the end of the duodenum tied off, for example by a purse string suture. Thereafter the instrument is closed in order to fire the staples so as to join the stomach to the duodenum. As is known, the instrument can then be removed through the opening originally made in the lumen of the stomach.

Where the circular anastomosis instruments are made with a center rod on which an anvil assembly can be threaded, it has been found that the threads may run the risk of tearing the tissue of the stomach when being aligned with or passed through the gastric wall, particularly where an opening which has been excised for the passage of the rod may be smaller than the center rod. Further, in order to provide an opening in the gastric wall, various types of excising devices have been used, for example along with a purse string-applicator. It is also known that the anvil must be aligned with a staple cartridge in the instrument so that an annular array of buckets on the anvil is aligned with the staples which are fired from the instrument during stapling. To this end, the anvil has been constructed of two parts. One part is provided with the buckets and is aligned with the center rod, for example, by means of a flat on the anvil being guided by a similar flat on the center rod. The second part is internally threaded and is rotatable in order to permit threading onto the center rod. However, threading of such an anvil onto a threaded center rod becomes somewhat subjective in that a surgeon may thread the anvil more or less onto therod. As a result, the distance between the anvil and the staple cartridge may vary from an optimum value.

Accordingly, it is an object of the invention to reduce the time required to use a circular type anastomosis stapler.

It is another object of the invention to provide a surgical staple apparatus which is capable of making an opening in tissue for a shaft of an anvil assembly.

It is another object of the invention to reduce the time required to create an anastomosis.

It is another object of the invention to reduce trauma to tissue when making an anastomosis.

It is an other object of the invention to precisely position a removable anvil on an anastomosis instrument.

Briefly, the invention provides a surgical stapler apparatus which is comprised of a tubular housing, a assembly for selectively mounting one of a trocar and an anvil assembly therein.

The tubular housing may be of any suitable construction. For example, the housing may form the distal end of a fixed shaft instrument or may form the distal end of a flexible shaft instrument.

The staple pusher assembly may be of any suitable construction and is movably mounted in the distal end of the housing for movement between a retracted position within the housing and an extended position for expelling an annular array of staples. In this respect, the annular array may include one or more annular rows of staples.

The means mounted within the staple pusher assembly for mounting a trocar or an anvil assembly includes at least one detent which is mounted for radial movement between a retaining position to hold a shaft of a trocar or a shaft of an anvil assembly and a release position to release the shaft of the trocar or anvil assembly. In this respect, the detent is spring biased to move from the release position into the retaining position.

In one embodiment, the means for mounting the trocar or the anvil assembly is in the form of a cylinder which is slidably mounted in the staple pusher assembly and which includes a central bore at a distal end to, receive the shaft of the selected trocar or anvil assembly and at least one longitudinally disposed slot in a side wall which communicates with the bore. In addition, the means includes at least one detent within the bore which is aligned with the slot for radial movement between a restraining position to hold the shaft in the cylinder and a release position within the slot to release the shaft.

The apparatus is also provided with an actuating means which is connected to the staple pusher assembly for moving the staple pusher assembly at least from the retracted position to the extended position in order to expel the staples. In addition, the apparatus includes a second actuating means which is connected to the means for selectively mounting a trocar or anvil assembly in order to move this means between a retracted position within the staple pusher assembly and an extended position relative to the staple pusher assembly in order to permit release of the received shaft. Both of these actuating means may be manipulated by a surgeon from the proximal end of the apparatus.

The trocar which is used may be of any suitable construction. Basically, the trocar includes a shaft which is provided with an annular recess at a proximal end in order to be engaged by one or more detents of the means for mounting the trocar within the tubular housing.

The anvil assembly is constructed with a shaft which is releasably mounted Within the housing and an anvil which is mounted on the shaft for facing the staple pusher assembly in order to clinch the expelled staples thereon. The shaft is also provided with a recess in order to be engaged by a detent of the mounting means in a manner as described above.

In addition, the anvil assembly includes an aligning means for aligning the shaft circumferentially within the mounting means in order to align an annular array of buckets on the anvil with staples in the staple pusher assembly. For example, the aligning means may include an annular shell liner within the tubular housing of the apparatus which has a plurality of internal circumferentially disposed longitudinal splines which cooperate with a plurality of external circumferentially disposed longitudinal splines on the shaft in order to align the shaft during insertion. For example, each of the splines of the shell as well as the shaft may be provided with a chamfered end for circumferentially guiding or turning the shaft during insertion.

The anvil assembly is also provided with a locking means for releaseably securing the anvil on the shaft. In this respect, the anvil includes a housing while the locking means includes a recess in the shaft, a spring in the housing which is at least partially disposed in the recess when locking the housing of the shaft and a latch which is movably mounted in the housing and which abuts against the spring in order to bias the spring out of the recess in response to movement of the latch to a release position. When the latch is in the release position and the spring has been moved out of the recess of the shaft, the housing can be slid off the shaft.

The anvil assembly also includes an aligning means for aligning the anvil housing in the shaft in order to align the annular array of buckets on the anvil with the staples in the staple pusher assembly.

When the surgical stapler apparatus is to be used, for example in forming an anastomosis between a stomach and a duodenum, the trocar is first mounted in the apparatus and moved into a retracted position. After passage of the distal end of the apparatus into the lumen of the stomach through a suitable opening, the surgeon manipulates the actuating means for moving the trocar into an extended position. At this time, the sharp distal end of the trocar can be exposed and used to pierce the gastric wall, for example within the confines of a previously applied purse string.

Thereafter, by further manipulation of the actuating means, the mounting means for the trocar can be further extended so that the mounting means is moved into a position to permit release of the trocar. Next, the trocar can be removed axially from the mounting means and the anvil assembly inserted. In this respect, either the entire anvil assembly can be inserted or only the shaft of the anvil assembly can be inserted. In any event, once the shaft has been inserted into the mounting means, the attached actuating means can be manipulated to draw the shaft into the tubular housing in order to retain the shaft in fixed relation with the housing.

In the event that the anvil assembly housing has not been previously mounted on the shaft, the housing can thereafter be slid over the distal end of the shaft and snap-locked in place by means of the spring therein engaging within the recess of the shaft. An anastomosis may then be created and the apparatus utilized in similar manner to conventional instruments of this type.

These and other objects advantages of the invention will become more apparent from the following detailed description taken in conjunction with the accompanying drawings wherein:

FIG. 1 illustrates a partially exploded view of a surgical stapler apparatus according to the invention passing through a gastric wall of a stomach;

FIG. 2 illustrates apart cross-sectional view of a distal end of the surgical stapler apparatus of FIG. 1 with a trocar mounted in place in accordance with the invention;

FIG. 3 illustrates a view similar to FIG. 2 with a trocar in an extended position for piercing tissue;

FIG. 4 illustrates a view similar to FIG. 3 in a position for removal of the trocar;

FIG. 5 illustrates a cross sectional view of the proximal end of the stapler apparatus with a shaft for an anvil assembly in place in a retracted position of the mounting means;

FIG. 6 illustrates a cross sectional view of an anvil assembly during initial insertion into the proximal end of the housing of the stapler apparatus in accordance with the inventions FIG. 7 illustrates a view similar to FIG. 6 with the anvil assembly in a retained position within the stapler housing;

FIG. 8 illustrates a view taken on line VIII—VIII of FIG. 6 with the locking means of the anvil assembly in locked position;

FIG. 9 illustrates a view similar to FIG. 8 with the locking means of the anvil assembly in an unlocked position;

FIG. 10 illustrates an exploded view of a shell liner for aligning the shaft of an anvil assembly in accordance with the invention; and FIG. 11 illustrates a view similar to FIG. 10 with the anvil assembly shaft being inserted into the shell liner.

Referring to FIG. 1, the surgical stapler apparatus 10 has an elongated shaft 11, for example of rigid or flexible type and is used, for example to create an anastomosis for a stomach 12. As indicated, the distal end of the apparatus 10 passes through an opening which has been surgically prepared in the stomach 12. In addition, a shaft 13 projects through an opening in the gastric wall 15 of the stomach 12 in order to receive an anvil 16.

Referring to FIG. 2, only the distal end of the apparatus 10 is illustrated since the remainder of the apparatus 10 is of generally conventional and well known construction. As illustrated, the apparatus 10 includes a tubular housing 17 which is formed of multiple parts. For example, the tubular housing 17 includes a cylinder 18, a shell liner 19 abutting the end of the cylinder 18, a shaped annular shell support 20 for securing the shell liner 19 to the end of the cylinder 18 and an enlarged mounting ring 21 which slides over the shell support 20. Suitable vent openings 22 are provided in a conical section of the mounting ring 21 for venting the interior of the housing 17, as is known. As indicated, the mounting ring 21 is sized so as to receive a staple cartridge 23 at the distal end. This cartridge 23 may be of suitable shape and may contain an array of staples 24, for example, two annular rows of staples.

The apparatus can also include a staple pusher assembly which is movably mounted in the distal end of the housing 10 for movement between a retracted position as shown within the housing 10 and an extended position for expelling the annular array of staples therefrom. In this respect, the assembly 25 includes a pusher 26 of conical shape having a plurality of vent openings 27 aligned with the openings 22 in the mounting ring 21. In addition, the assembly 25 includes an annular ring 27 from which a plurality of pusher fingers or drivers 28 extend auxiliary and in alignment with the staples 24 in the cartridge 23. In addition, an annular blade 29 is mounted coaxially within the pusher fingers 28.

The staple pusher assembly also includes a quill 30 of cylindrical shape which is slidably mounted within the cylinder 18 of the housing 17. This quill 30 has arcuate fingers at the distal end which pass through suitable openings 31 in the shell liner 19 so as to abut the pusher 26. A suitable actuating means 32 is connected to the quill 30 in order to move the pusher assembly 25 from a retracted position illustrated in FIG. 2 to an extended position (not shown) for expelling of the staples 24.

The apparatus 10 also has means mounted within the staple pusher assembly 25 for selectively mounting either a trocar 33 as shown in FIG. 2 or an anvil assembly 13, 16 as indicated in FIGS. 1 and 6. This means includes a cylinder 34 which is slidably mounted within the quill 30 of the pusher assembly 25. The cylinder 34 is provided with a central bore 35 which extends from the distal end inwardly to an intermediate point of the cylinder 34. In addition, at least one pair of longitudinal diametrically opposed slots 36 are provided in a side wall of the cylinder 34 to communicate with the bore 35. In addition, a spring means in the form of a discrete U-shaped spring 37 is disposed within the bore 35 and aligned with the slots 36. In this respect, the spring 37 has a base 38 which is mounted within a bottom section of the bore 35 so as to be retained within the confines of the bore 35. The spring 37 also has a pair of arms 39 extending from the base 38 in alignment with the respective slots 36. Each arm 39 carries a detent 40 at the distal end which is aligned with a slot 36 for radial movement between a retaining position to hold the trocar 33 therein (FIG. 2) or the anvil assembly 13, 16 (FIG. 5) and a release position to release the trocar 33 (FIG. 4) or the anvil assembly 13, 16.

Referring to FIG. 2, a sleeve 41 of stainless steel or the like is tightly fitted over the cylinder 34 and abuts against the shell liner 19 in order to hold the spring arms 39 in the restraining position as shown. This sleeve 41 is of harder material than the spring arms 39 to ensure sliding in and sliding out of the arms 39 during use of the apparatus. A coiled spring 42 is also disposed about the cylinder 34 and is recessed within the quill 30 to bias the sleeve 41 against the shell liner 19. This spring 42 permits relative movement between the sleeve 41 and the quill 30 when the quill 30 is moved as described below.

As indicated in FIG. 2, the trocar 33 has a shaft 41' which is provided with an annular recess 42' into which the detents 40 of the spring 37 engage. In addition, the trocar 33 has a sharp tip for piercing tissue. For example, the tip may be provided with a two stage chamfer, that is, with a distal section 33a forming a steeper angle relative to the axis of the trocar 33 than an immediately following section 33b. This provides a sharper point for initially piercing tissue.

In addition, the trocar 33 may be coated with a radiopaque material, such as barium sulfate, for locating the trocar 33 within a section of tissue, if necessary, using X-ray equipment or the like.

Referring to FIG. 3, an actuating means 43 is connected to the proximal end of the cylinder 34 in order to effect movement of the cylinder 34 between a retracted position as shown in FIG. 2 and a fully extended position as illustrated in FIG. 4. As indicated, the actuating means 43 is in the form of a set of interengaging bands one end of which is fixed within a slot at the proximal end of the cylinder 34 by means of a pair of pins 44 which pass through the cylinder 34.

Referring to FIG. 5, the shaft 13 of the anvil assembly includes a mounting means at the proximal end, for example, in the form of an annular recess 45 in order to receive the dotonus of the spring 37. In addition, the proximal end of the shaft 13 is formed with a conical tip for aligning of the shaft 13 into the cylinder 34 or for acting as a trocar if needed for entry of the anvil assembly into a tube of tissue. In addition, an aligning means is provided for aligning the shaft 13 circumferentially within the housing 17. In this respect, as indicated in FIGS. 10 and 11, the aligning means includes a plurality of external circumferentially disposed longitudinal splines 47 on the shaft 13 and internal splines 46 in the shell 19. In addition, each of the splines 46 of the shell 19 has a chamfered distal end while the splines 47 on the shaft are chamfered and sloped such that when the splines 47 of the shaft 13 are initially inserted into the shell lines 19, the chamfered ends of the splines 46, 47 serve to rotate the shaft 13 slightly as indicated in FIG. 11 to ensure that the splines 46, 47 mate properly for reasons as described below.

Referring to FIG. 6, the anvil 16 is slidably mounted on the shaft 13 at the distal end and includes an anvil plate 48 in which an annular array of buckets 49 are provided in the face facing the staple cartridge 23. In addition, the anvil 16 includes a two-part housing including an annular anvil support body 50 on which the anvil plate 48 is fixedly mounted and an anvil tip 51 which is fixedly mounted on the support body 50 as by a cement or adhesive.

The anvil support body 50 includes an aligning means for aligning the body of the shaft 13 in order to position the buckets 49 in one of a plurality of positions, that is, in alignment with the staples 24 of the cartridge 23. In this respect, the aligning means includes a plurality of internal splines 53 on the support body 50 which mate with the splines 47. As noted above, the splines 47 at the proximal end of the shaft 13 serve to align the shaft with the shell liner 19 and, thus, the pusher fingers 28. The cartridge 23 Is, in turn, aligned with the pusher fingers 28. The splines 52, 53 (FIG. 5) are arranged so that the buckets 49 can be aligned with the staples 24.

The anvil 16 also includes a locking means releasably securing the anvil 16 to the shaft 13. To this end, a backing plate 54 of a generally rectangular shape with arcuate ends is mounted in a like recess of the support body 50 at the distal end. The plate 54 is provided with a central opening 55 of a diameter greater than the diameter of a reduced distal end of the shaft 13. When the anvil 16 is in a locked position, the backing plate 54 is aligned with an annular recess 56 in the reduced end of the shaft 13.

The locking means also includes a spring 57 which slides on the backing plate 54 and is at least partially disposed in the recess 56 in order to lock the support body 50 on the shaft 13 As indicated in FIGS. 8 and 9, the spring 57 is of U-shape with a pair of legs 58 which are disposed in the recess 56 when in a locked position. A spring-biased latch 59 is movably mounted in the anvil tip 51 in abutting relationship with the spring 57 as indicated in FIG. 8. In addition, the latch 59 is recessed at the proximal end to receive the legs 58 of the spring 57 and has a central abutment wall 60 which serves as a cam surface for the legs 58 of the spring.

Referring to FIG. 9, when the latch 59 is moved into the anvil tip 51, that is into a released position, the abutment wall 60 of the latch 59 spreads the legs 58 of the spring so as to disengage from the recess 56 of the shaft. At this time, the two-part anvil 16 can be slid off the shaft 13.

As illustrated in FIG. 6, the distal end of the shaft 13 can be provided with a conical head 61 to facilitate passage of the spring legs 58 thereover when the anvil 16 is being mounted on the shaft 13. Also, the shaft 13 may be provided with a reduced diameter section or annular groove 62 adjacent the anvil 16 to accommodate a purse string or tissue bunching caused by drawing in of a purse string.

As indicated, the tip 51 is provided with a somewhat spherical shape at the distal end in order to provide smooth surfaces for insertion into body tissue such as a duodenum and for manipulation into and out of a bowel or other tissue.

In use, the surgical stapler apparatus 10 can be initially provided with a trocar 33 disposed in a recessed position within the staple pusher assembly 25 as indicated in FIG. 2. In this position, the shaft 41' of the trocar 33 is held by the intents 40 at the ends of the spring 37 such that the shaft 41' cannot be moved axially out of the cylinder 34. In this respect, as indicated in FIG. 2, the legs 39 of the spring 37 are spread apart into the slots 36 of the cylinder 34 so that the spring cannot move axially out of the bore 35 of the cylinder 34. At the same time, the legs 39 abut against the sleeve 41 so that radial outward movement of the legs 39 is prevented.

After the apparatus has been passed through an opening into the lumen of a stomach 12, this urge on manipulates the actuating means 43 so as to move the cylinder 34 into a partially extended position as illustrated in FIG. 3. In this position, the pointed tip of the trocar 33 passes axially beyond the tubular housing 17 so as to pierce the gastric wall 15 which is illustrated as being layered. At the same time, the cylinder 34 moves relative to the quill 30 and sleeve 41 with the spring legs 39 still being retained against radial outward movement by the shell liner 19 and the pusher 26. That is, the shaft 41' of the trocar is still held in a retained position.

Referring to FIG. 4 after an opening has been made in the gastric wall 15, the actuating means 43 is further manipulated to further extend the cylinder 34 so that the legs 39 of the spring 37 are free to move radially outwardly to permit release of the shaft 41 of the trocar 33. The trocar 33 can then be suitably gripped and removed from the apparatus 10 through the opening provided in the gastric wall 15. After removal of the trocar shaft 41, the detents 40 of the spring 37 are biased to move back into the restraining position, as viewed Referring to FIG. 5, the shaft 13 of the anvil assembly can then be inserted into the cylinder 34 with the detents 40 of the spring 37 snapping into place in the annular recess 45 of the shaft 13. Thereafter, the actuating means 43 is manipulated to draw the cylinder 34 back into the quill 30. At this time, when the splines 47 on the shaft 13 approach the internal splines 46 of the shell liner 19, the chamfered ends of the splines 46, 47 cause a slight rotation of the shaft 13 if the splines 45, 47 are not otherwise disposed in a mating interfitting relationship.

After the cylinder 34 has been retracted into the retracted position, as indicated in FIG. 5, the shaft is ready to receive the anvil 16 as indicated in FIG. 1. At this time, the anvil is snapped over the shaft 13.

Referring to FIG. 6, when the anvil 16 is being slid onto the shaft 13, the splines 52, 53 serve to align the support body 50 and thus the buckets 49 with the staples 24 in the cartridge 23. An anastomosis may then be completed in known manner, for example, with the anvil tip 51 being inserted into via duodenum (not shown).

Of note, the entire anvil assembly, that is, the anvil 16 and shaft 13 can be inserted into the cylinder 34 as a single unit where desired.

Further, the anvil assembly may be inserted into a duodenum or other suitable lumen prior to insertion into the cylinder 34. In this respect, the duodenum or lumen can be closed about the anvil 16, with only the shaft 13 being exposed. The shaft 13 can then be inserted into the cylinder 34 for engagement by the spring detents 40 in a manner as described above. The actuating means 43 can then be manipulated in order to draw the anvil assembly and duodenum into position for an anastomosis as indicated in FIG. 7.

Once the anvil assembly 13, 16 has been positioned for an anastomosis, the actuating means 32 for the staple pusher assembly can be actuated to expel the staples 24 while causing the annular blade 29 to cut the usual "donut". Thereafter, the apparatus can be removed from the anastomosis site in the usual fashion.

The invention thus provides a surgical stapler apparatus which is capable of making its own aperture via a removable trocar and of subsequently receiving an anvil assembly for stapling purposes.

Further, the invention provides an anvil assembly in which an anvil can be rapidly and easily mounted in place without heed for a threading action.

Further, the apparatus permits an anastomosis to be created with a limited number of instruments and limited operational procedures. As a result, an anastomosis can be created in a minimum of time.

The invention also provides an anvil which can be snapped into a fixed position in a rapid manner and the position can be accurately located in relation to the staples of a staple cartridge.

Further, where appropriate, a surgeon may release the anvil from the anvil shaft after an anastomosis has been formed in order to facilitate removal of the apparatus. Thereafter, the anvil can be removed through the tissue.

What is claimed is:

1. A surgical apparatus for applying fasteners comprising:
   a tubular housing having a longitudinal axis and a movable shaft positioned therein;
   an anvil assembly removably mounted to said movable shaft, said anvil assembly including an anvil head and an anvil shaft; and
   a detent mechanism for removably mounting said anvil shaft to said movable shaft, said detent mechanism including at least one detent positioned for movement between first and second positions, wherein in said first position said at least one detent prevents release of said anvil shaft from said movable shaft and in said second position said at least one detent allows release of said anvil shaft from said movable shaft.

2. A surgical apparatus as set forth in claim 1, wherein said movable shaft is movable between a retracted position and an extended position, said at least one detent retained in said first position when said movable shaft is in said retracted position.

3. A surgical apparatus as set forth in claim 2, wherein said at least one detent is spring biased to said first position.

4. A surgical apparatus as set forth in claim 3, wherein movement of said movable shaft to said retracted position pulls said anvil shaft proximally, and a cylindrical member positioned within said tubular housing prevents movement of said at least one detent radially outwardly.

5. A surgical apparatus as set forth in claim 2, wherein removal of said anvil shaft from said movable shaft initially forces said at least one detent in a direction away from said longitudinal axis.

6. A surgical apparatus as set forth in claim 1, wherein said detent mechanism comprises two radially movable detents positioned opposite one another, said detents protruding towards said longitudinal axis of said tubular housing.

7. A surgical apparatus as set forth in claim 6, wherein said detents are spring biased inwardly towards the longitudinal axis.

8. A surgical apparatus as set forth in claim 7, wherein mounting of said anvil shaft to said movable shaft initially forces said detents radially outwardly.

9. A surgical apparatus as set forth in claim 8, wherein said anvil shaft comprises a recess to receive said detents.

10. A surgical apparatus as set forth in claim 1, further comprising a trocar portion extending proximally from said anvil shaft, said trocar portion having an annular recess to receive said at least one detent.

11. A surgical apparatus for applying fasteners comprising:
a tubular housing having a longitudinal axis and a movable shaft positioned therein for sliding movement relative to the tubular housing;
an anvil assembly having a shaft removably mounted to said movable shaft;
a retaining mechanism for removably mounting said anvil assembly to said movable shaft, said retaining mechanism including a pair of longitudinally extending spring biased elongated arms, each of said elongated arms having a protruding portion extending inwardly towards said longitudinal axis, said protruding portion movable radially between an inner and an outer position with respect to said longitudinal axis to allow removal of said anvil assembly.

12. A surgical apparatus as set forth in claim 11, wherein said elongated arms are normally in said inner position and removal of said anvil assembly forces said elongated arms to said outer position.

13. A surgical apparatus as set forth in claim 12, wherein said movable shaft is movable between a retracted and an extended position, said elongated arms being maintained in said inner position when said movable shaft is in said retracted position.

14. A surgical apparatus for applying fasteners comprising:
a tubular housing having a longitudinal axis and a movable shaft;
an anvil assembly including an anvil head and an elongated anvil shaft extending therefrom, said anvil head having an annular row of fastener forming buckets, said anvil shaft removably mounted to said movable shaft;
a fastener pusher assembly including an annular row of fasteners positioned opposite the anvil head and a longitudinally sliding fastener pusher; and
a plurality of splines positioned on an outer surface of said anvil shaft for aligning said annular row of anvil buckets with said annular row of fasteners when said anvil shaft is mounted to said movable shaft.

15. A surgical apparatus as set forth in claim 14, wherein said anvil shaft has a longitudinal axis and said splines extend substantially parallel to said longitudinal axis.

16. A surgical apparatus as set forth in claim 15, further comprising a plurality of internal splines positioned within said tubular housing to mate with said splines on said anvil shaft.

17. A surgical apparatus as set forth in claim 16, wherein said anvil shaft has a distal end adjacent said anvil head and a proximal end, said splines on said anvil shaft being spaced from said proximal end.

18. A surgical apparatus as set forth in claim 16, wherein said internal splines are positioned adjacent a distal end portion of the tubular housing.

19. A surgical apparatus as set forth in claim 14, further comprising a retaining mechanism for preventing removal of said anvil shaft from said movable shaft when in a retracted position.

20. A surgical apparatus for applying fasteners comprising:
a tubular housing having a longitudinal axis and a movable shaft;
a fastener pusher assembly positioned at a distal end of said tubular housing and including an annular row of fasteners;
a trocar extending from said movable shaft for penetrating body tissue, said trocar movable between a retracted position wherein said trocar is prevented from penetrating tissue and an extended position wherein said trocar protrudes from said tubular housing to penetrate tissue in a first direction;
an anvil assembly including an anvil head and an anvil shaft extending therefrom, said anvil shaft having a proximal end and a distal end and removably positioned along the longitudinal axis of the tubular housing; and
a trocar tip extending from said distal end of said anvil shaft for penetrating body tissue from a second direction, said second direction being opposite said first direction.

21. A surgical apparatus as set forth in claim 20, wherein in said retracted position, said trocar is positioned entirely within said tubular housing.

22. A surgical apparatus as set forth in claim 21, wherein said trocar is removably mounted to said movable shaft.

23. A surgical apparatus for applying fasteners comprising: a tubular housing having proximal and distal ends, and a longitudinal axis;
an anvil assembly including an anvil head and an anvil shaft extending therefrom;
a plurality of fasteners positioned opposite said anvil head;
a fastener pusher for ejecting the fasteners; and
a movable shaft positioned within said tubular housing for movement between first and second positions, said anvil shaft removably mounted to said movable shaft, wherein movement of said movable shaft to a retracted position prevents release of the anvil shaft and movement of said movable shaft to an extended position allows release of the anvil shaft from the movable shaft, said movable shaft pulling said anvil shaft toward said retracted position when moved toward said second position.

24. A surgical apparatus as set forth in claim 23, wherein said movable shaft is longitudinally slidable within said tubular housing.

25. A surgical apparatus as set forth in claim 24, wherein said anvil shaft has a plurality of splines extending substantially parallel to the longitudinal axis.

26. A surgical apparatus as set forth in claim 23, wherein said anvil shaft is snap fit to said movable shaft.

27. A surgical apparatus as set forth in claim 26, further comprising a detent mechanism, said detent mechanism movable between first and second positions to prevent removal of said anvil shaft.

* * * * *